United States Patent [19]
Carson et al.

[11] Patent Number: 5,674,452
[45] Date of Patent: Oct. 7, 1997

[54] HOLLOW FIBER EXCHANGERS

[75] Inventors: Gary A. Carson, Golden; Robert E. Doty, Lakewood; Michael R. Hoglund, Thornton, all of Colo.; James D. Isaacson, Sandy, Utah

[73] Assignee: Cobe Laboratories, Lakewood, Colo.

[21] Appl. No.: 548,048

[22] Filed: Oct. 25, 1995

Related U.S. Application Data

[62] Division of Ser. No. 261,308, Jun. 16, 1994, Pat. No. 5,489,413, which is a continuation of Ser. No. 50,641, Apr. 22, 1993, abandoned, which is a continuation-in-part of Ser. No. 970,781, Nov. 3, 1992, Pat. No. 5,470,531.

[51] Int. Cl.$^6$ .................. A61M 1/14; A61M 1/34
[52] U.S. Cl. .................. 422/46; 422/48; 210/321.76; 210/321.84; 210/645; 604/4
[58] Field of Search .................. 422/46, 48; 210/321.76, 210/321.84, 645; 604/4

[56] References Cited

U.S. PATENT DOCUMENTS

| Re. 32,186 | 6/1986 | Bentley | 210/646 |
|---|---|---|---|
| Re. 33,932 | 5/1992 | Fukasawa et al. | |
| 3,370,710 | 2/1968 | Bluemle, Jr. | |
| 3,422,008 | 1/1969 | McLain | 210/321 |

(List continued on next page.)

FOREIGN PATENT DOCUMENTS

| 1190443 | 7/1985 | Canada. |
|---|---|---|
| 0041467A1 | 12/1981 | European Pat. Off. |
| 0 080 661A1 | 8/1983 | European Pat. Off. |
| 0 089 122 | 9/1983 | European Pat. Off. |

(List continued on next page.)

OTHER PUBLICATIONS

Hot Plate Welders, Ultrasonic Welders, Spin Welders, Vibration Welders, Thermo Stakers, Leak Testers; Sales Brochure, Forward Technology Industries Inc., Minneapolis, Minnesota, Jun. 1991.

Pall Blood Filter Brohcure, Pall Corporation, 1984.

Primary Examiner—Nina Bhat
Attorney, Agent, or Firm—Finnegan, Henderson, Farabow, Garrett, & Dunner, L.L.P.

[57] ABSTRACT

An exchanger includes an outer casing having an inlet port and an outlet port for a first fluid, and an inlet port and an outlet port for a second fluid, and a bundle of hollow fibers located within the outer casing and being in flow communication with the inlet and outlet port for the second fluid. A central core is located in the outer casing and the bundle of fibers is arranged around the central core. The central core includes an inlet manifold connected to the first fluid inlet port, and an outlet manifold connected to the first fluid outlet port.

12 Claims, 8 Drawing Sheets

U.S. PATENT DOCUMENTS

| | | |
|---|---|---|
| 3,489,647 | 1/1970 | Kolobow . |
| 3,536,611 | 10/1970 | de Filippi et al. ............................ 422/46 |
| 3,690,465 | 9/1972 | McGinnis et al. ......................... 210/321 |
| 3,788,482 | 1/1974 | Markley . |
| 3,794,468 | 2/1974 | Leonard ...................................... 422/46 |
| 3,998,593 | 12/1976 | Yoshida et al. ............................. 422/46 |
| 4,023,699 | 5/1977 | Lien ........................................... 220/287 |
| 4,028,252 | 6/1977 | Morris . |
| 4,030,629 | 6/1977 | Melnikov .................................... 220/211 |
| 4,111,659 | 9/1978 | Bowley ...................................... 422/48 |
| 4,138,464 | 2/1979 | Lewin ........................................ 422/46 |
| 4,140,637 | 2/1979 | Walter . |
| 4,163,721 | 8/1979 | Lobdell . |
| 4,172,794 | 10/1979 | Sigdell . |
| 4,196,075 | 4/1980 | Bentley . |
| 4,199,457 | 4/1980 | Esmond . |
| 4,219,422 | 8/1980 | Knothe et al. . |
| 4,228,125 | 10/1980 | Lobdell et al. . |
| 4,237,091 | 12/1980 | Lobdell et al. . |
| 4,239,625 | 12/1980 | Hlavinka . |
| 4,239,729 | 12/1980 | Hasegawa et al. ......................... 422/48 |
| 4,246,121 | 1/1981 | Corbin, III et al. . |
| 4,267,044 | 5/1981 | Kroplinski et al. . |
| 4,306,018 | 12/1981 | Kirkpatrick . |
| 4,346,006 | 8/1982 | Kopp et al. . |
| 4,352,736 | 10/1982 | Ukai et al. . |
| 4,368,124 | 1/1983 | Brumfield . |
| 4,376,095 | 3/1983 | Hasegawa . |
| 4,394,567 | 7/1983 | Epstein et al. ............................. 219/306 |
| 4,424,190 | 1/1984 | Mather, III et al. . |
| 4,431,539 | 2/1984 | Brosanyi . |
| 4,451,562 | 5/1984 | Elgas et al. . |
| 4,455,230 | 6/1984 | Elgas et al. . |
| 4,469,659 | 9/1984 | Carson et al. . |
| 4,622,206 | 11/1986 | Torgeson . |
| 4,645,645 | 2/1987 | Martinez et al. . |
| 4,656,004 | 4/1987 | Stewart . |
| 4,657,743 | 4/1987 | Kanno . |
| 4,663,125 | 5/1987 | Gordon et al. . |
| 4,698,207 | 10/1987 | Bringham et al. . |
| 4,735,775 | 4/1988 | Leonard et al. . |
| 4,791,054 | 12/1988 | Hamada et al. . |
| 4,818,490 | 4/1989 | Carson et al. . |
| 4,863,600 | 9/1989 | Leonard et al. . |
| 4,863,603 | 9/1989 | Lehmann et al. . |
| 4,876,066 | 10/1989 | Bringham et al. . |
| 4,886,193 | 12/1989 | Wassilief ................................... 222/446 |
| 4,923,679 | 5/1990 | Fukasawa et al. . |
| 4,929,254 | 5/1990 | Meyering et al. . |
| 4,940,617 | 7/1990 | Baurmeister . |
| 4,950,391 | 8/1990 | Weickhardt . |
| 4,975,247 | 12/1990 | Badolato et al. . |
| 5,034,188 | 7/1991 | Nakanishi et al. . |
| 5,124,127 | 6/1992 | Jones et al. ................................ 422/46 |
| 5,143,312 | 9/1992 | Baurmeister . |
| 5,192,499 | 3/1993 | Sakai et al. ................................ 422/46 |
| 5,230,862 | 7/1993 | Berry et al. ................................ 422/48 |
| 5,335,806 | 8/1994 | Dedoes ...................................... 220/358 |
| 5,376,334 | 12/1994 | Haworth et al. .......................... 422/46 |
| 5,377,859 | 1/1995 | Hacker ...................................... 220/287 |

FOREIGN PATENT DOCUMENTS

| | | |
|---|---|---|
| 0093677A1 | 11/1983 | European Pat. Off. . |
| 0122022 | 10/1984 | European Pat. Off. . |
| 0167162 | 1/1986 | European Pat. Off. . |
| 243796A2 | 11/1987 | European Pat. Off. . |
| 0285993 | 10/1988 | European Pat. Off. . |
| 0 292 398 | 11/1988 | European Pat. Off. . |
| 292445 | 11/1988 | European Pat. Off. . |
| 318993 | 6/1989 | European Pat. Off. . |
| 373847A3 | 6/1990 | European Pat. Off. . |
| 0380307 | 8/1990 | European Pat. Off. . |
| 0506212A2 | 9/1992 | European Pat. Off. . |
| 0285812B1 | 10/1993 | European Pat. Off. . |
| 2643268 | 8/1990 | France . |
| 2300312 | 7/1973 | Germany . |
| 244133A1 | 12/1973 | Germany . |
| 2721444A1 | 11/1978 | Germany . |
| 2825065 | 12/1979 | Germany . |
| 3304353A1 | 12/1983 | Germany . |
| 207607 | 3/1984 | Germany . |
| 3236946A1 | 12/1984 | Germany . |
| 233946A1 | 3/1986 | Germany . |
| 243857A1 | 3/1987 | Germany . |
| 37 07 584.5 | 1/1988 | Germany . |
| 38 03 693.2 | 3/1988 | Germany . |
| 264381A1 | 2/1989 | Germany . |
| 4123125A1 | 1/1993 | Germany . |
| 52-23577 | 2/1977 | Japan . |
| 55-48844 | 12/1980 | Japan . |
| 1481064 | 7/1977 | United Kingdom . |
| 2063706 | 6/1981 | United Kingdom . |
| WO82/00102 | 1/1982 | WIPO . |
| WO 96/02914 | 5/1986 | WIPO . |

HOLLOW FIBER EXCHANGERS

RELATED APPLICATIONS

This is a division of application Ser. No. 08/261,308, filed Jun. 16, 1994 now U.S. Pat. No. 5,489,413 which is a continuation of U.S. application Ser. No. 08/050,641 filed Apr. 22, 1993, now abandoned, which is a Continuation-in-Part of application Ser. No. 07/970,781 filed Nov. 3, 1992 now U.S. Pat. No. 5,470,531.

BACKGROUND OF THE INVENTION

1. Field of the Invention

The invention relates to hollow fiber membrane exchangers. While the invention is subject to a wide range of applications, it is especially suited for use in oxygenating blood and will be particularly described in that connection.

2. Description of the Related Art

During open heart surgery, natural cardiovascular activity is suspended, which causes the lungs to collapse. It is therefore necessary to simulate the function of the lungs, which replaces carbon dioxide in the blood with oxygen. Blood oxygenators serve this function. A typical hollow fiber blood oxygenator includes a bundle of hollow fibers extending through a blood chamber for conveying oxygen into the blood chamber and for removing carbon dioxide from the blood therein. Specifically, the fibers are constructed of a membrane material that acts as a boundary between extracorporeal blood flow and oxygen flow. As blood flows on the outside of the fibers and oxygen passes through the hollow fibers, a gas exchange occurs wherein oxygen passes through the fiber walls and into the blood and carbon dioxide passes, in the opposite direction, from the blood into the interior of the hollow fibers.

There are multiple and sometimes conflicting parameters that must be considered when designing a hollow fiber membrane exchanger. For example, the longer blood remains in contact with the fibers, the greater the amount of gas exchange that may occur. Thus, it may be desirable to design the oxygenator so that the length of the flow path of the blood relative to the hollow fibers is maximized to thereby maximize contact between blood and the hollow fibers. On the other hand, it is desirable to construct an exchanger that is as small and compact as possible. Thus, the desire to build a compact unit is somewhat constrained by blood flow path length requirements.

Biocompatibility is also a factor that must be considered in exchanger design. For example, membrane exchangers are typically manufactured from multiple components that are joined together with adhesives. However, in order to minimize the possibility of bioincompatibility between the blood and the materials that make up the exchanger, it is preferable to minimize the number of materials with which extracorporeal circulating blood comes into contact. Thus, while adhesives may be necessary, it is beneficial to limit the amount of adhesive that is located in the blood flow path.

Finally, gas exchange requirements, which are often dependent upon a particular use, also place constraints on the ultimate design of an exchanger. For example, adults typically have greater gas exchange requirements than children, and therefore require a larger membrane compartment. Therefore it is common for manufacturers to offer exchangers of varying sizes, each size being designed for a particular gas exchange requirement, and each size employing its own uniquely sized parts. However, this is not cost effective. From a cost efficiency perspective, it is easier to develop economies of scale if many of the same parts can be used regardless of the membrane size. Thus, it is preferable to provide a membrane exchanger that is constructed of as many standard parts as possible for use with membranes of varying sizes.

SUMMARY OF THE INVENTION

An advantage of the invention is to provide an exchanger that maximizes the time during which extracorporeally circulating blood contacts the hollow fibers while at the same time minimizing the size of the exchanger.

Another advantage of the invention is to provide an exchanger which minimizes possibility of bioincompatibility.

A further advantage of the invention is to provide an exchanger that can be manufactured economically in different sizes.

Additional features and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purposes of the invention, as embodied and broadly described herein, the invention comprises an exchanger including an outer casing having an inlet port and an outlet port for a first fluid, and an inlet port and an outlet port for a second fluid. A bundle of hollow fibers is located within the outer casing, and is in flow communication with the inlet port and the outlet port for the second fluid. A central core is located in the outer casing and the bundle of fibers is arranged around the central core. The central core includes an inlet manifold connected to the first fluid inlet port, and an outlet manifold connected to the first fluid outlet port.

Preferably the central core has a substantially elongated tubular shape and the inlet and outlet manifolds are recessed in the core and extend along substantially the entire length of the core.

It is also preferable for the outer casing and central core to be sized and shaped so that the bundle of fibers sandwiched therebetween varies in density, the bundle having a lower density in areas adjacent the inlet and outlet manifolds than in areas spaced from the inlet and outlet manifolds.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention, and together with the description, serve to explain the principles of the invention.

DESCRIPTION OF THE PREFERRED EMBODIMENTS

Reference will now be made in detail to the present preferred embodiments of the invention, an example of which is illustrated in the accompanying drawings. Wherever possible, like reference numerals are used to designate the same or like parts.

Figure 1:
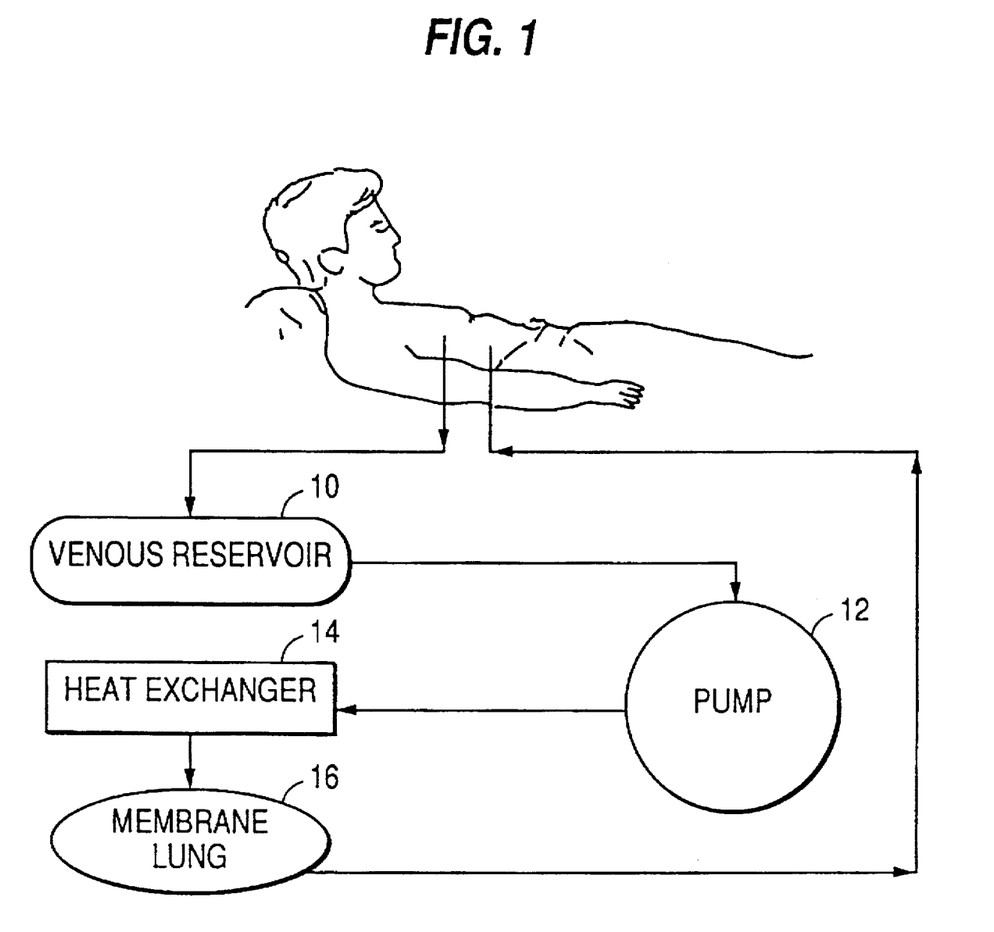
FIG. 1 schematically illustrates the typical interconnection of a patient to a membrane exchanger such as the exchanger of the present invention.

When the membrane exchanger of the present invention is used to oxygenate blood and remove carbon dioxide therefrom, the exchanger may be connected to a patient under treatment in a manner illustrated in FIG. 1.

As illustrated in FIG. 1, blood tubing is connected between the venous system of a patient and venous reservoir 10. A blood pump 12 conveys blood from reservoir 10 to heat exchanger 14. In the heat exchanger, the temperature of the blood is altered to reach a desired treatment temperature and the blood is then conveyed to a membrane lung 16, which, in the case of the present invention is a hollow fiber oxygenator. From membrane lung 16, the treated blood is returned to the arterial system of the patient. In this manner the patient's gas exchange needs and body temperature can be regulated during complex procedures such as cardiovascular bypass surgery.

Figure 2:
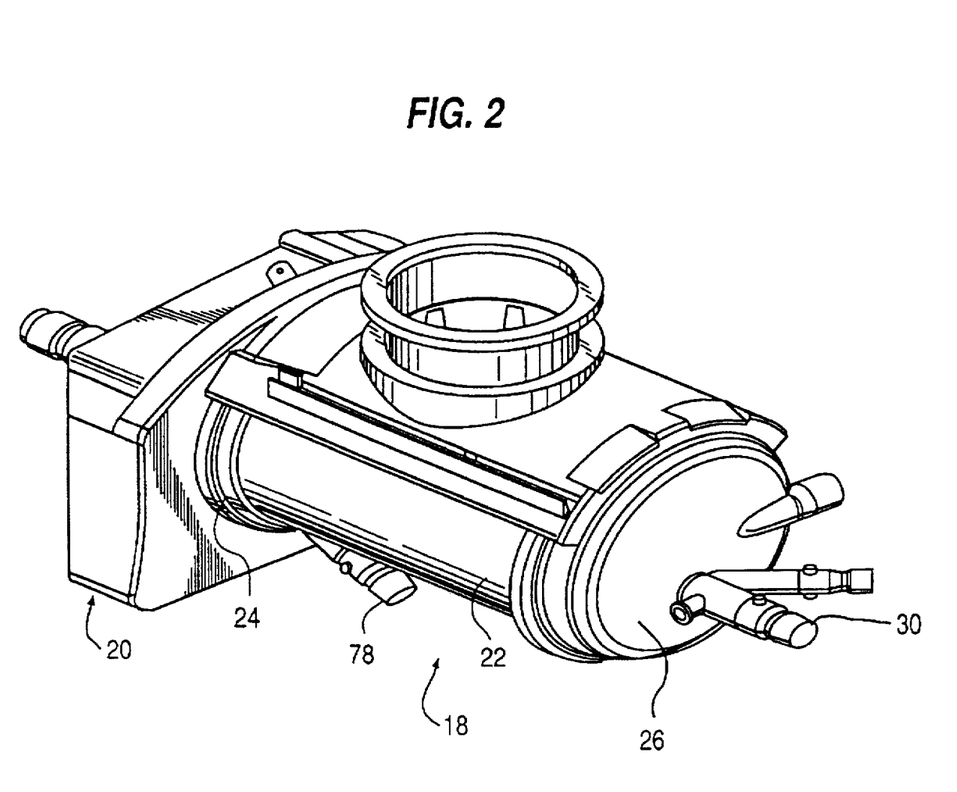
FIG. 2 is an oblique drawing of a membrane exchanger module and interconnected heat exchanger module in accordance with the present invention.

The present invention provides an apparatus for accomplishing these vital gas exchange and temperature regulation needs. As illustrated in FIG. 2, a preferred embodiment of the invention includes oxygenation module 18 and heat exchanger module 20.

Figure 3:
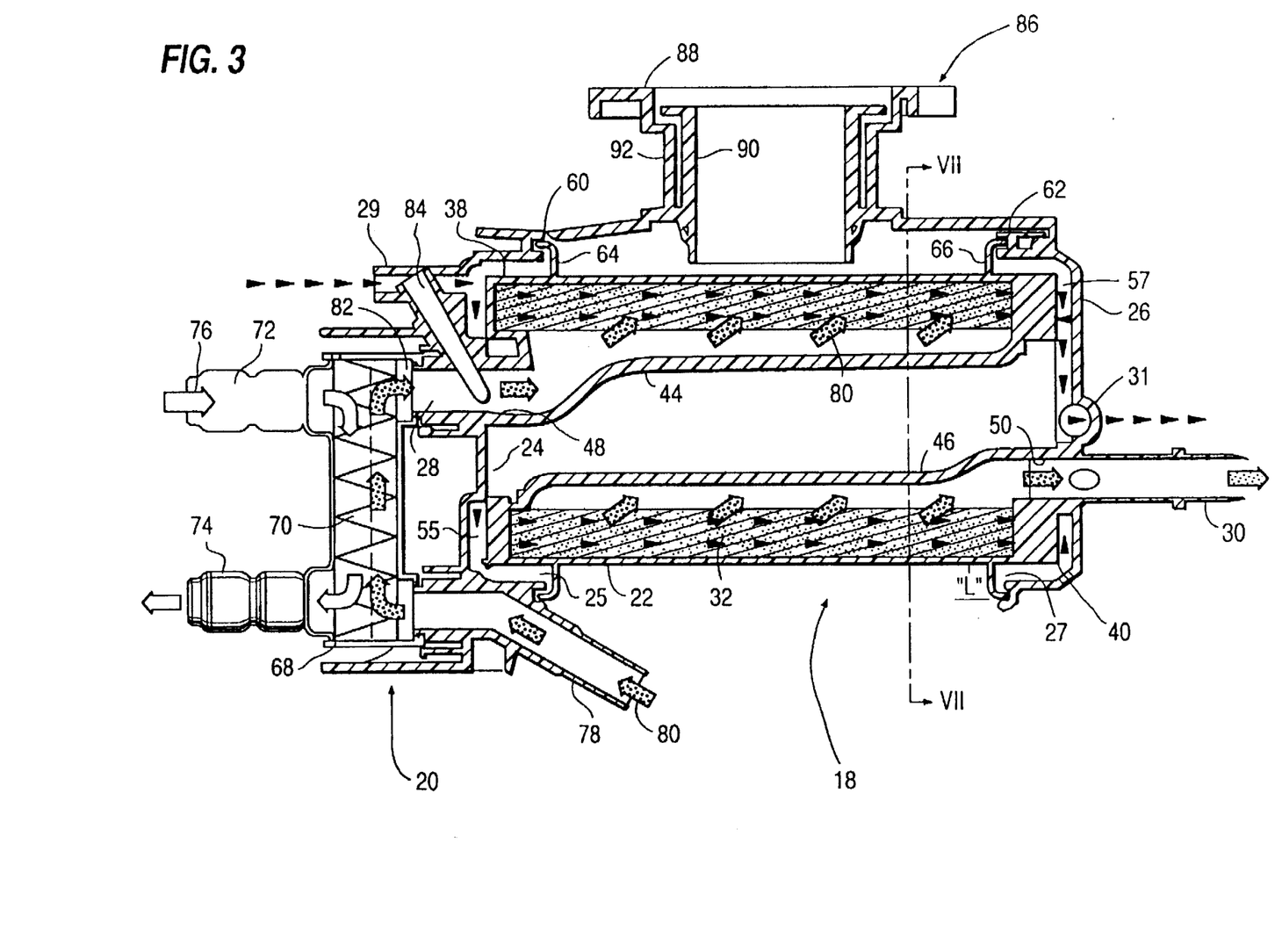
FIG. 3 is a cross-sectional front view of the apparatus illustrated in FIG. 2.

In accordance with the present invention there is provided a gas exchanger having an outer casing with an inlet port and an outlet port for a first fluid, and an inlet port and outlet port for a second fluid. As illustrated in FIGS. 2 and 3, the outer casing includes a substantially cylindrical outer tube 22 which is preferably constructed of a transparent plastic material. The outer casing also includes an inlet cap 24 and an outlet cap 26, disposed on opposite ends of tube 22. Inlet cap 24 includes a first fluid inlet port 28 located therein for permitting a first fluid to enter the interior of oxygenation module 18. The first fluid may exit oxygenation module 18 through outlet port 30 located in outlet cap 26. Additionally, a second fluid inlet port 29 is provided in inlet cap 24, and a second fluid outlet port 31 is provided in outlet cap 26. When the invention is used in connection with blood oxygenation, the first fluid is blood which enters and exits exchanger module 18 through ports 28 and 30, respectively, and the second fluid is oxygen which enters and exits module 18 through ports 29 and 31, respectively. Ports 28 and 30 include inwardly tapered male ends extending toward the inside of cap 24 and 26.

Figure 9:
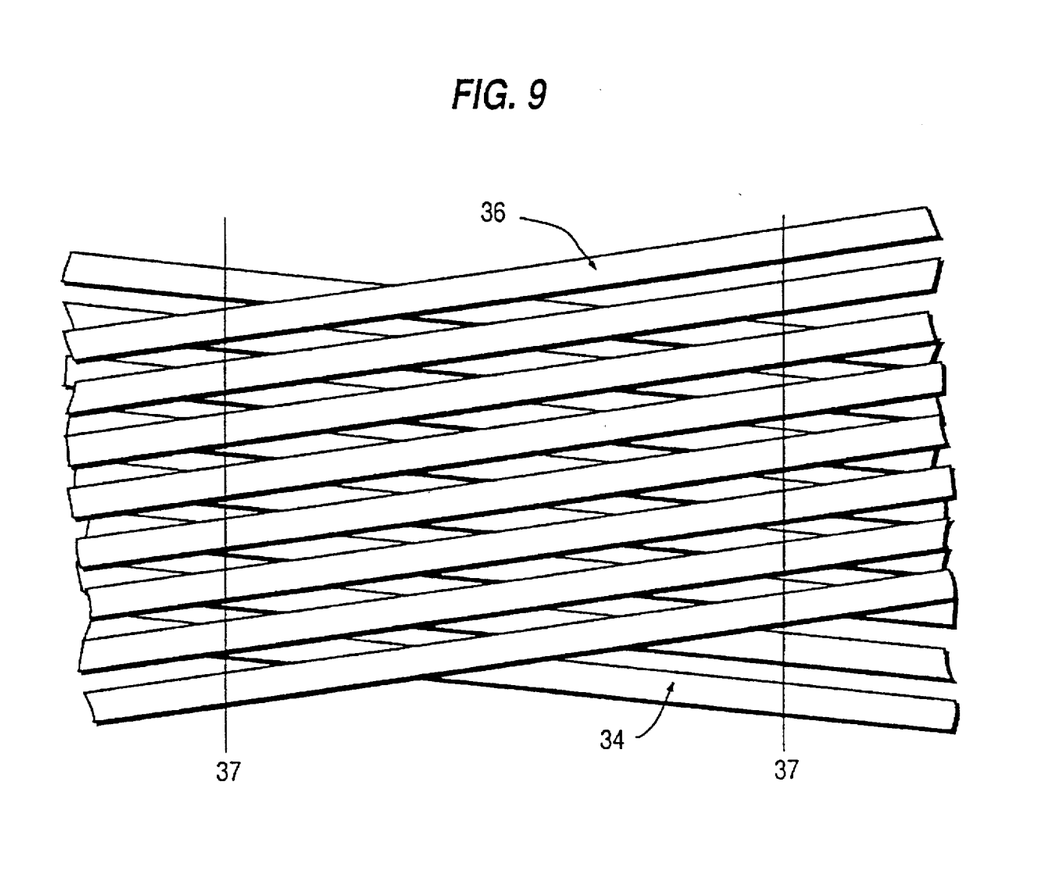
FIG. 9 illustrates fiber orientation of the bundle of hollow fibers illustrated in FIG. 3.

In accordance with the present invention there is also provided a bundle of hollow fibers located within the outer casing and being in flow communication with the inlet port and the outlet port for the second fluid. As embodied herein and as illustrated in FIG. 3, a bundle of hollow fibers 32 is arranged in a tubular formation within outer tube 22. As illustrated in FIG. 9 the fiber bundle consists of a double layer, cross-wound hollow fiber mat of which is rolled upon itself to form the bundle illustrated in cross-section in FIG. 3. Each of the layers of fibers 34, 36 includes a plurality of fibers arranged in parallel and stitched together with parallel stitching 37 to limit the fibers movement relative to each other. The fibers of adjacent layers of mats 34, 36 are angled with respect to each other to prevent adjacent layers 34, 36 from nesting within one another. For example, the fibers of one mat may define an angle of 22° with respect to the fibers of the other mat. The ratio of the distance between two adjacent lines of stitching 37 to the distance between two adjacent fibers may be about 45.

Many different types of hollow fiber may be employed, depending upon desired use. In a preferred embodiment for use in a blood oxygenator, the fibers may be constructed of polypropylene microporous material, each fiber having an outer diameter of about 380 μm and an inner diameter of 280 μm. An acceptable average density may be approximately 14.3 fibers per centimeter. After the mats 34, 36 are rolled to form bundle 32 and each fiber is closed at both ends by pinching, the ends 38, 40 of bundle 32 are potted within tube 22 using a resin to thereby seal the fibers together at their ends and to seal bundle 32 within tube 22. After the resin dries, the ends 38, 40 are shaved to reopen the fibers so that fluid, such as oxygen may flow therethrough.

In accordance with the invention there is also provided a central core located within the outer case, and around which the bundle of fibers is arranged, the central core including an inlet manifold connected to the first fluid inlet port and an outlet manifold connected to the first fluid outlet port.

Figure 4:
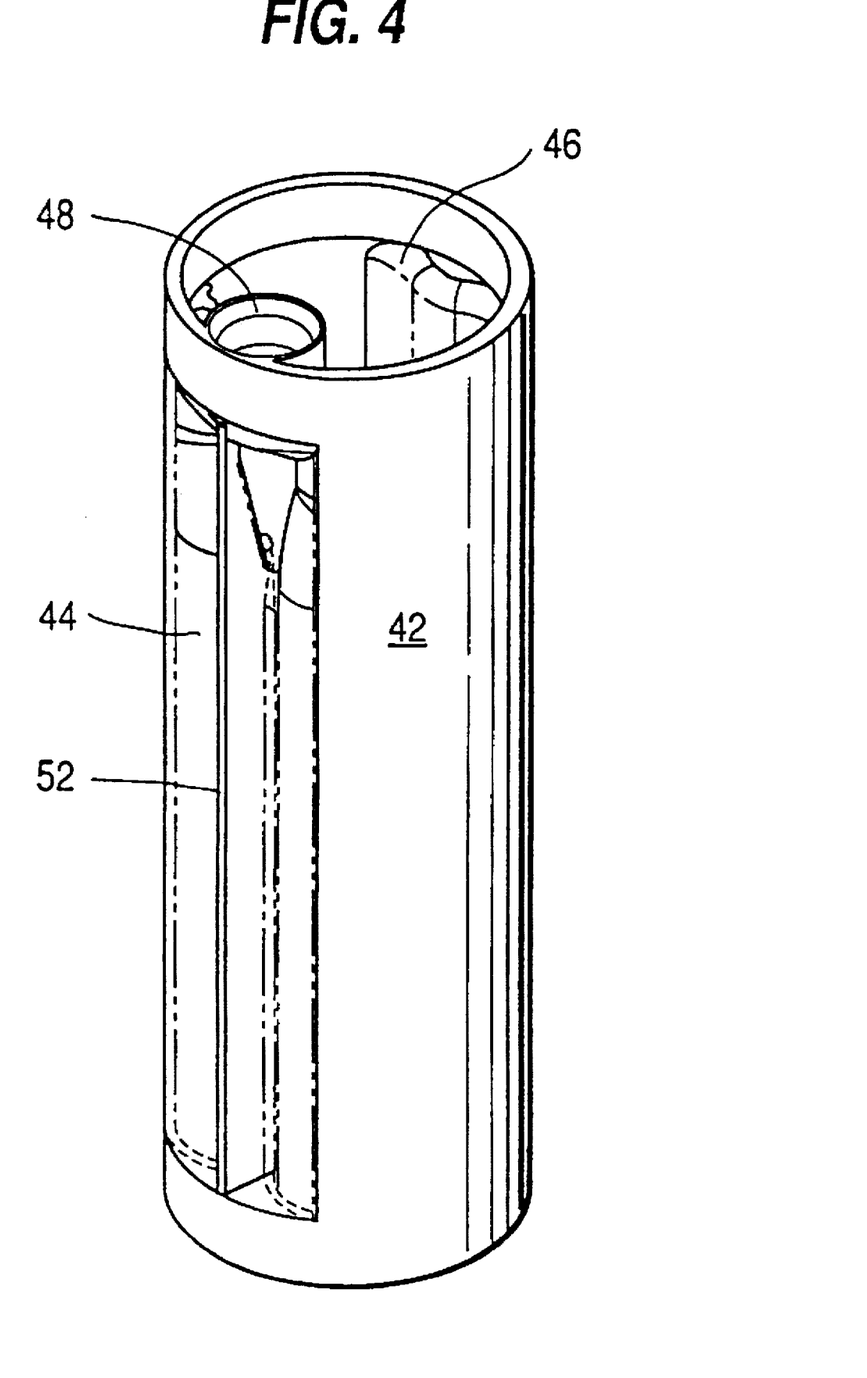
FIG. 4 is an oblique view of the core illustrated in FIG. 3.
Figure 5:
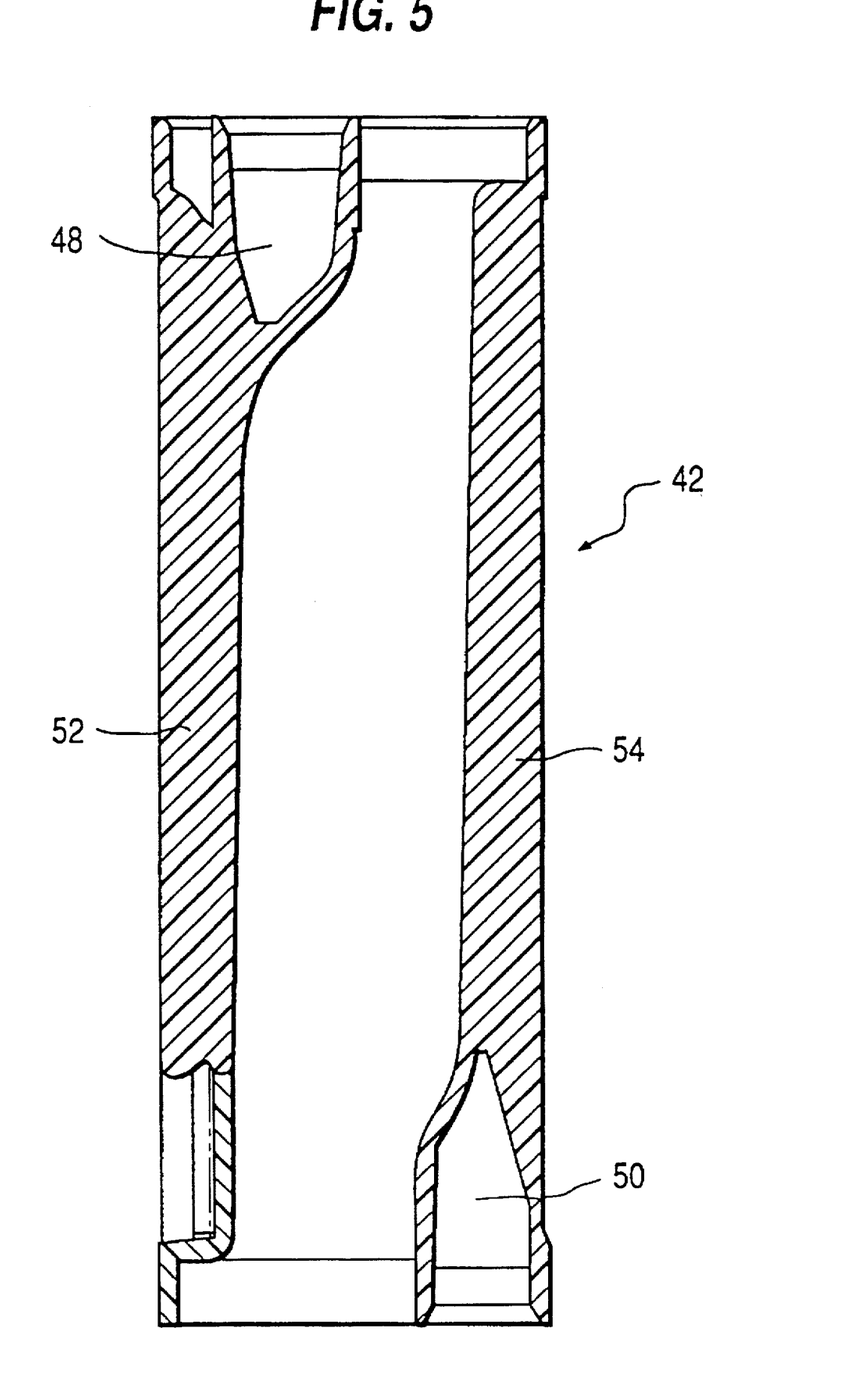
FIG. 5 is a cross-sectional view of the core illustrated in FIG. 4.
Figure 6:
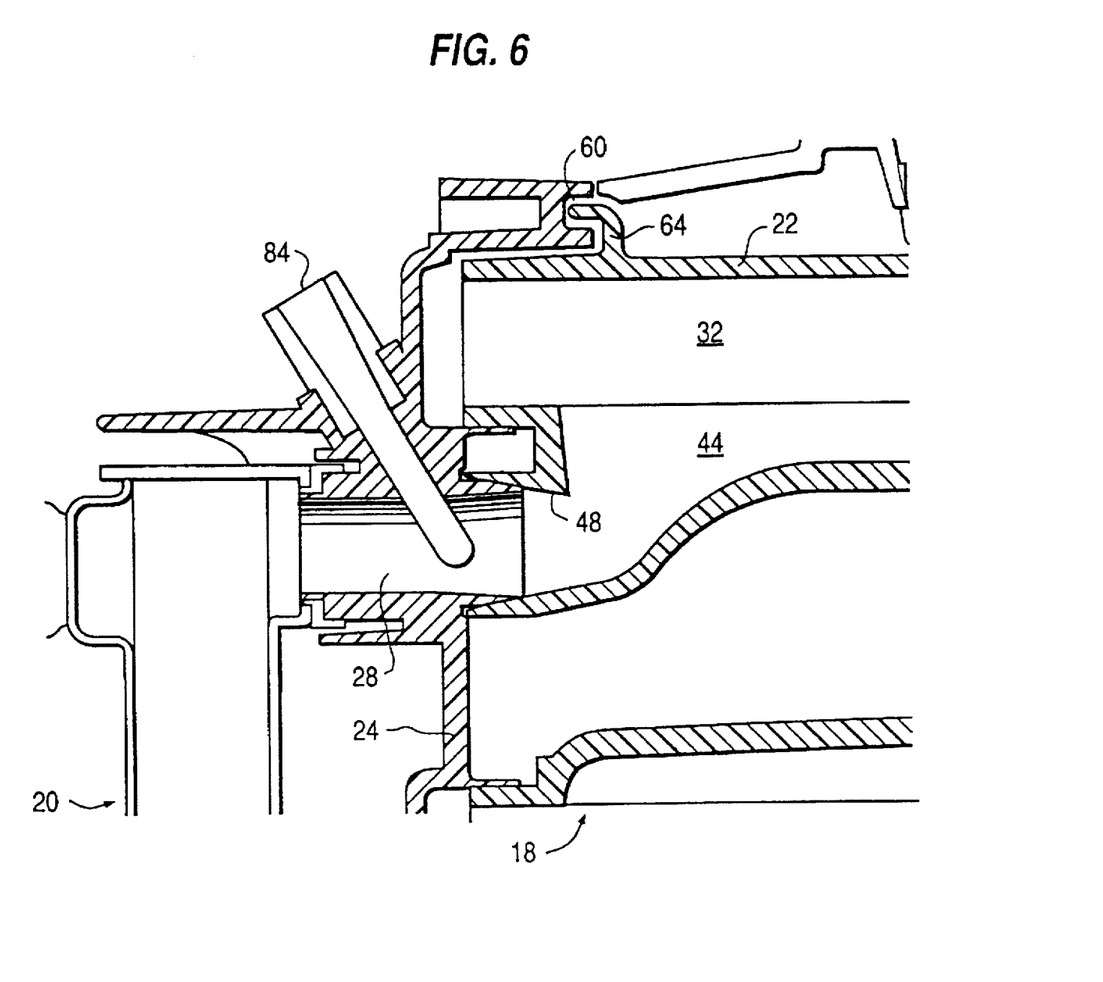
FIG. 6 is an enlarged detail of a portion of FIG. 3.

As embodied herein, and as best illustrated in FIGS. 4, 5, and 6, central core 42 includes inlet manifold 44 and outlet manifold 46. Central core 42 has a generally cylindrical tubular shape, with manifolds 44 and 46 being recessed in central core 42 in a diametrically opposed orientation and each manifold extending towards the central axis of core 42. The location of manifolds 44 and 46 within the center portion of the core conserves space and enhances blood flow through hollow fiber bundle 32, as is described later in greater detail.

Inlet manifold 44 and outlet manifold 46 each include a generally V-shaped concavity extending substantially along the length of core 42. A pair ports 48 and 50 are located within core 42 and are respectively connected to inlet manifold 44 and outlet manifold 46. Ports 48 and 50 each include an outwardly tapered apertures for respectively receiving inwardly tapered male ends of first fluid inlet port 28 and first fluid outlet port 30, previously described. Ports 28 and 48 mate in a press-fitting relationship so that no adhesive is required to join the ports. Similarly, ports 30 and 50 engage each other in a press-fit manner.

Manifolds 44 and 46 each include central ribs 52 and 54 that run the length of their respective manifold and which each include distal edges which are recessed from the outer diameter of central core 42, as is indicated by the dashed lines in FIG. 6. In other words the outside of the core surface defines an arc, and the distal edges of the ribs are located below this arc. Ribs 52 and 54 include apertures 56 and 58 (as best illustrated in FIG. 5) respectively located in the regions of inlet port 48 and outlet port 50. Apertures 50 and 56 enhance even blood flow on opposite sides of ribs 52 and 54.

The double fiber mat previously described is wrapped around core 42 in order to form hollow fiber bundle 32 and is sandwiched between core 42 and tube 22. The previously described potting on ends 38 and 40 of bundle 32 seal the ends between core 42 and tube 22. Caps 24 and 26 are respectively spaced from potted ends 38 and 40 to define circular gas inlet and outlet manifolds 55 and 57, respectively.

Figure 7:
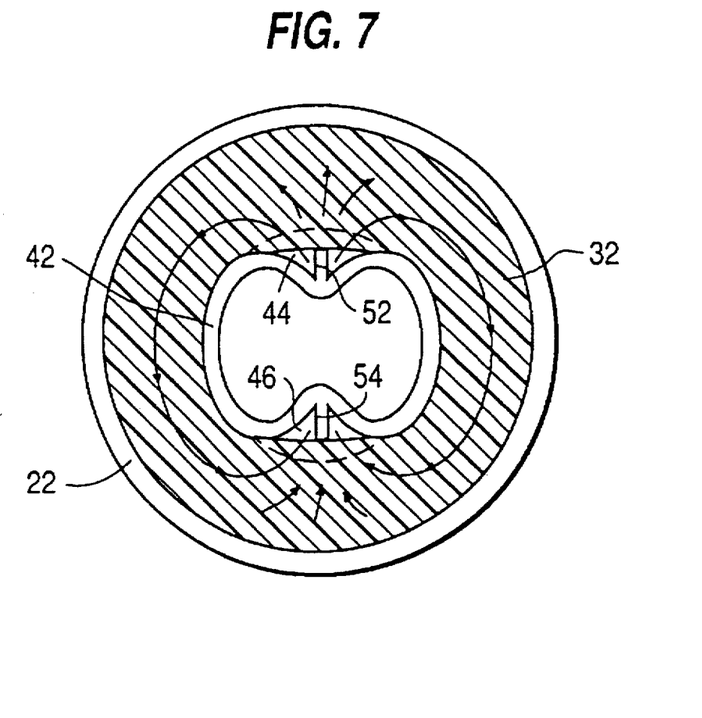
FIG. 7 is a cross-sectional side view taken along the line VII—VII in FIG. 3 where the cross-sectional blood flow pattern is illustrated.

As illustrated in FIG. 7, the concave nature of manifolds 44 and 46 in combination with the previously described recessed nature of ribs 52 and 54 provide reduced support for hollow fiber bundle 32 in the regions of the manifolds 44 and 46. Thus, the fiber density in the regions immediately surrounding and above the concavities of the manifolds 44 and 46 is less than the fiber density in all other areas of the bundle. This reduced manifold region bundle density enhances even absorption of blood into the fiber bundle as blood exits the inlet manifold, enhances even return of blood to the outlet manifold, and generally provides a more even distribution of blood through the bundle of hollow fibers.

The invention may also include connecting means for sealing at least one of caps 24 and 26 to outer tube 22. As embodied herein the connecting means may be any type of conventional or non-conventional structure including grooves, adhesives or mechanical connections. Preferably, the connecting means includes angled circumferentially disposed flanges 64 and 66 extending from tube 22, and corresponding ridges 60 and 62 in caps 24 and 26. An advantage of this preferred embodiment of the invention is that varying capacity exchangers may be manufactured from many of the same components, thereby obviating the need to manufacture and stock many different parts for different capacity exchangers. Specifically, if a manufacturer wishes to construct exchangers with varying thickness hollow fiber bundles, other than the amount of membrane itself, the only structure that need be varied is the outer tube 22. This feature results from the central orientation of the inlet and outlet manifolds, as well as the unique seal of the preferred connecting means between outer tube 22 and caps 24 and 26. Specifically, caps 24 and 26 are oversized relative to outer tube 22 so that annular spaces 25 and 27 are formed between the outer wall of tube 22 and the inner wall of caps 24 and 26. Each of caps 24 and 26 include annular grooves 60 and 62, respectively. Corresponding angled flanges 64 and 66 extend from outer tube 22 and mate with annular grooves 60 and 62. Resin is deposited about grooves 60 and 62 to seal the circumferential angled flanges 64 and 66 within grooves 60 and 62, respectively. Thus, a leakproof seal is attained between caps 24, 26 and tube 22.

With this arrangement, a manufacturer can construct exchangers of varying capacity using a standard sized inner core 42 and caps 24 and 26. In order to accommodate a thicker hollow fiber membrane bundle, an outer tube 22 of greater diameter is used, which includes angled flanges 64 and 66 which are decreased by the same amount of the tube diameter increase so that the angled flanges mesh with grooves 60 and 62 of caps 24 and 26, respectively. Likewise, if an exchanger with a smaller capacity hollow fiber bundle is desired, the diameter of outer tubing 22 is decreased, and the radial length "L" (as shown in FIG. 3) of flanges 64 and 66 are increased by the same amount. Thus, the preferred embodiment of the invention maximizes the number of interchangeable parts between varying capacity exchangers, thereby making it easier for a manufacturer to achieve economies of scale.

The exchanger configuration of the invention with its centrally oriented core permits a blood oxygenator to be molded as a single unit which is an advantage from both a manufacturing and a safety point of view. Specifically, since the core is formed of a single molded part, it includes no bonds which would be necessary if the core was made from more than one part. Elimination of such bonds is beneficial since they are susceptible to leakage under pressure.

The present invention may also include a heat exchanger module 20 integrally connected with exchanger module 18. The purpose of heat exchanger module 20 is to control the temperature of the fluid being treated. Specifically, when the invention is used in connection with oxygenation of blood during cardiovascular bypass surgery, heat exchanger module 20 is used to regulate the temperature of the patient's blood. This is accomplished by providing a heat exchanger casing 68 which is divided into two separate compartments by a folded heat conducting sheet 70. Heat conducting sheet 70 may be constructed of stainless steel, metal foil, or any other suitable heat conducting material. Heat exchange inlet port 72 and heat exchange outlet port 74 permit a heat exchange fluid to flow along a first side of the folded foil membrane 70 as indicated by arrows 76. Blood inlet port 78 permits blood to flow on an opposite side of foil membrane 70 as indicated by arrows 80. As heat exchange fluid and blood pass along opposite sides of sheet 70, a heat exchange takes place across sheet 70, and the temperature of the blood is altered. Blood outlet 82 of heat exchanger module 20 is directly connected to blood inlet port 28 of exchanger module 18. A stainless steel thermometer well 84 extends into the blood flow path adjacent heat exchanger outlet port 82 so that blood temperature may be monitored during the medical procedure.

The invention may employ any type of conventional heat-exchanger and, in its broadest sense, the invention need not include heat exchanger module 20 integrally connected with exchanger module 18. However, the fixed interconnection is preferred because it reduces the number of tubing hook-ups required during the medical procedure, thereby minimizing the possibilities of leakage and contamination. In addition, the direct interconnection shortens the overall length of the extracorporeal blood circuit.

Another feature of the invention which permits a shortening of the extracorporeal blood circuit includes pivotal venous reservoir mount 86 located atop gas exchanger module 18. Mount 86 includes a table 88 having a rotatable mounting tube 90 extending therefrom. Mounting tube 90 rotates within a collared bracket 92 which is fixed to gas exchange module 18. This structure permits the venous reservoir to be maintained in the closest possible proximity to the exchanger, thereby limiting the required length of blood tubing between the venous reservoir and the exchanger.

Figure 8:
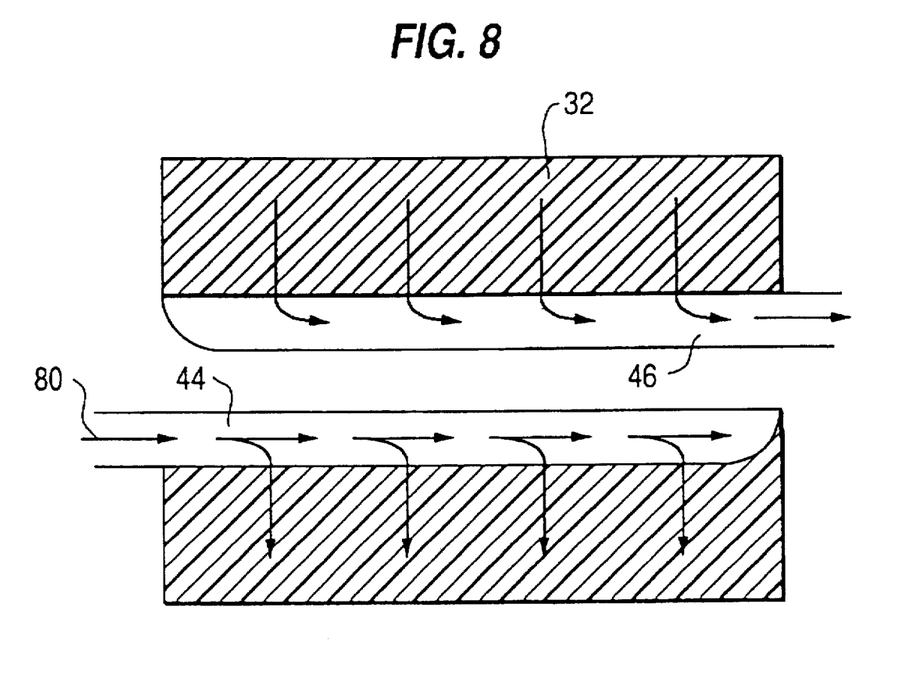
FIG. 8 illustrates the cross-sectional blood flow pattern as occurs in the cross-sectional view of FIG. 3.

Operation of the invention will now be described with references to FIGS. 3, 7, and 8. Initially, a venous reservoir (not shown) is placed on rotatable mount 86, and is connected through a pump to inlet port 78 of heat exchanger module 20. Ports 72 and 74 of heat exchanger module 20 are connected to a heat exchange fluid circuit (not shown). The venous reservoir is also connected to the vascular system of a patient, and blood outlet port 30 is connected to the vascular system of a patient.

After the apparatus is primed in a conventional manner, treatment is commenced by flowing blood from the venous reservoir into blood inlet port 78 of heat exchanger module 20. As the blood passes along one side of folded sheet 70 within heat exchanger module 20, heat exchange fluids simultaneously passes along an opposite side of folded sheet 70 to alter the temperature of the blood. This temperature is monitored by a temperature probe (not shown) which is disposed in well 84. Blood then exits heat exchanger module 20 through outlet port 82 and enters gas exchange module 18 through inlet port 28 in cap 24. Blood then flows into inlet manifold 44, and enters hollow fiber bundle 32 at an angle transverse to the radius of bundle 32, as indicated by arrows 80. As indicated by the arrows in FIGS. 7 and 8, the blood flow path of the blood through bundle 32 is maximized in as much as the blood flows not only from the inner diameter to the outer diameter of core 32, but also flows halfway around the circumference of core 32 where it is collected in outlet manifold 46.

Simultaneously, oxygen enters the apparatus through gas inlet port 29 where it enters the potted inlet end 38 of hollow fiber bundle 32. Oxygen then passes through the hollow fibers of the bundle and is released into the blood as blood flows around the fibers of bundle 32. As oxygen enters the blood, carbon dioxide exits the blood and enters the interior of the hollow fibers. The carbon dioxide then passes through the potted outlet end 40 of hollow fiber bundle 32 and exits the apparatus through gas outlet port 31. In this manner, temperature regulation and gas exchange of a fluid such as blood may be achieved.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An exchanger, comprising:

an outer casing having a tubular outer wall;

an angled flange connected to and extending from the outer casing, the flange having a generally L-shaped cross-section and including a wall extending substantially parallel to the outer wall of the casing and being circumferentially spaced therefrom, the flange wall having a distal end;

at least one cap located on an end of the outer casing, the cap having a wall extending substantially parallel to the outer wall of the casing and being circumferentially spaced therefrom;

a central core;

a bundle of hollow fibers arranged around the central core and positioned directly between the outer wall the central core;

a circumferential groove located in an edge of the cap wall for receiving the distal end of the flange wall.

2. The exchanger of claim 1 further including resin disposed in the groove.

3. The exchanger of claim 1 wherein the cap engages both the distal end of the flange wall and the central core.

4. The exchanges of claim 3 wherein the cap engages the central core in a press-fitting relationship.

5. The exchanger of claim 1 wherein the central core includes a blood inlet port, a blood inlet manifold connected to the blood inlet port, a blood outlet port, and a blood outlet manifold connected to the blood outlet port.

6. The exchanger of claim 1 wherein a circumferential angled flange is disposed on opposite ends of the outer wall and a cap is located on each of said opposite ends.

7. The exchanger of claim 1 wherein said at least one cap includes two caps, each cap being located on an opposite end of the tubular outer wall.

8. An exchanger having one of a plurality of capacities, comprising:

an outer casing having a tubular outer wall with an outer casing diameter, the outer casing diameter being different for each of the plurality of capacities and having an angled circumferential flange extending therefrom by a radial length, the radial length being different for each of the plurality of capacities;

a bundle of fibers located within the outer casing;

a central core having a central core diameter less than the outer casing diameter located in the outer casing and around which the bundle of fibers is arranged, a thickness of the bundle of fibers; and a cap having a cap diameter located on an end of the outer casing, the cap having a wall extending substantially parallel to the outer wall of the casing and being spaced radially therefrom; wherein the outer casing diameter and the radial length cooperate to cause the wall of the cap to engage the angled flange; and wherein each of the plurality of capacities of the exchanger is defined by the difference between the outer casing diameter and the central core diameter.

9. An apparatus as claimed in claim 8, wherein the wall of the cap includes a circumferential groove that receives a portion of the angled flange.

10. An apparatus as claimed in claim 9, wherein resin is disposed in the groove.

11. An apparatus as claimed in claim 8, wherein the central core includes a blood inlet port, a blood inlet manifold connected to the blood inlet port, a blood outlet port, and a blood outlet manifold connected to the blood outlet port.

12. An apparatus as claimed in claim 8, further including a heat exchanger integrally connected thereto and having an outlet port which is flow connected to an interior portion of the outer casing.

* * * * *

UNITED STATES PATENT AND TRADEMARK OFFICE
CERTIFICATE OF CORRECTION

PATENT NO. : 5,674,452
DATED : October 7, 1997
INVENTOR(S) : Gary A. Carson, et al.

It is certified that error appears in the above-indentified patent and that said Letters Patent is hereby corrected as shown below:

Claim 1, Column 7, line 45, after "outer wall" insert -- and --.

Signed and Sealed this

Ninth Day of December, 1997

Attest:

BRUCE LEHMAN

Attesting Officer   Commissioner of Patents and Trademarks